(12) United States Patent
Son et al.

(10) Patent No.: US 12,377,413 B2
(45) Date of Patent: Aug. 5, 2025

(54) BLOOD BRAIN BARRIER-ON-A-CHIP

(71) Applicants: UNIVERSITY-INDUSTRY COOPERATION GROUP OF KYUNG HEE UNIVERSITY, Yongin-si (KR); SEOUL NATIONAL UNIVERSITY R&DB FOUNDATION, Seoul (KR)

(72) Inventors: Young-Sook Son, Seoul (KR); Su-Min Kim, Seoul (KR); Noo Li Jeon, Seoul (KR); Somin Lee, Seoul (KR); Minhwan Chung, New Haven, CT (US)

(73) Assignees: UNIVERSITY-INDUSTRY COOPERATION GROUP OF KYUNG HEE UNIVERSITY, Yongin-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 664 days.

(21) Appl. No.: 17/217,037

(22) Filed: Mar. 30, 2021

(65) Prior Publication Data

US 2022/0297117 A1 Sep. 22, 2022

(30) Foreign Application Priority Data

Mar. 22, 2021 (KR) ........................ 10-2021-0036821

(51) Int. Cl.
*B01L 3/00* (2006.01)
*C12M 1/42* (2006.01)
(Continued)

(52) U.S. Cl.
CPC ............ *B01L 3/5027* (2013.01); *C12M 21/08* (2013.01); *C12M 23/16* (2013.01); *C12M 35/08* (2013.01);
(Continued)

(58) Field of Classification Search
CPC ............. B01L 3/5027; B01L 2200/027; B01L 2300/0861; C12M 21/08; C12M 23/16;
(Continued)

(56) References Cited

U.S. PATENT DOCUMENTS

2011/0244567 A1* 10/2011 Jeon ..................... B01D 9/0054
435/395
2017/0355945 A1* 12/2017 Kamm .................. C12M 21/08

FOREIGN PATENT DOCUMENTS

| CN | 108823145 A | * 11/2018 | ........... C12N 5/0697 |
| EP | 2526978 B1 | 12/2020 | |
| KR | 10-2013-0013119 A | 2/2013 | |

* cited by examiner

*Primary Examiner* — Liban M Hassan
(74) *Attorney, Agent, or Firm* — Sughrue Mion, PLLC

(57) ABSTRACT

Disclosed is a blood-brain barrier vascular network implemented in a microfluidic chip. The blood-brain bather vascular network structure (BBB on a chip) (in vitro blood-brain bather (BBB)-on-a chip) formed in a microfluidic chip manufactured by a present manufacturing method of the in vitro blood-brain barrier (BBB)-on-a chip may reconstruct the blood-brain barrier in a real human body more similarly due to a specific cell configuration, compared to the conventional in vitro blood-brain barrier (BBB)-on-a chip, and thus may be used as a more accurate in vitro blood-brain barrier, and may be used for the development of various cellular therapeutic agents or drugs that work in the treatment of various brain diseases.

8 Claims, 9 Drawing Sheets

(51) Int. Cl.
  *C12M 3/00* (2006.01)
  *C12M 3/06* (2006.01)
  *G01N 33/483* (2006.01)
(52) U.S. Cl.
  CPC .... *G01N 33/4833* (2013.01); *B01L 2200/027* (2013.01); *B01L 2300/0861* (2013.01); *G01N 2500/02* (2013.01)
(58) Field of Classification Search
  CPC ............... C12M 35/08; G01N 33/4833; G01N 2500/02; G01N 33/5008; G01N 2500/00
  See application file for complete search history.

[FIG 1]
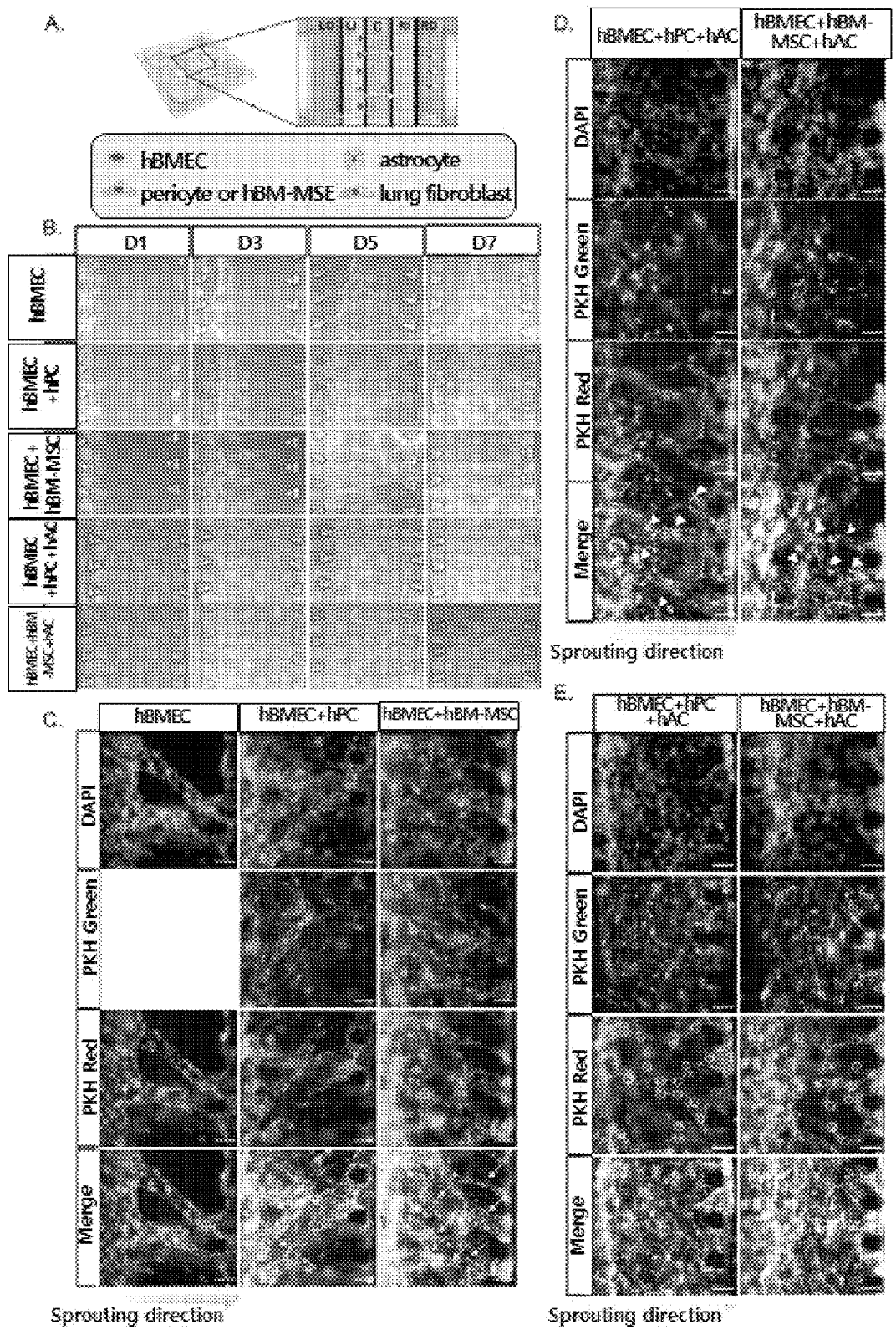

[FIG 2]
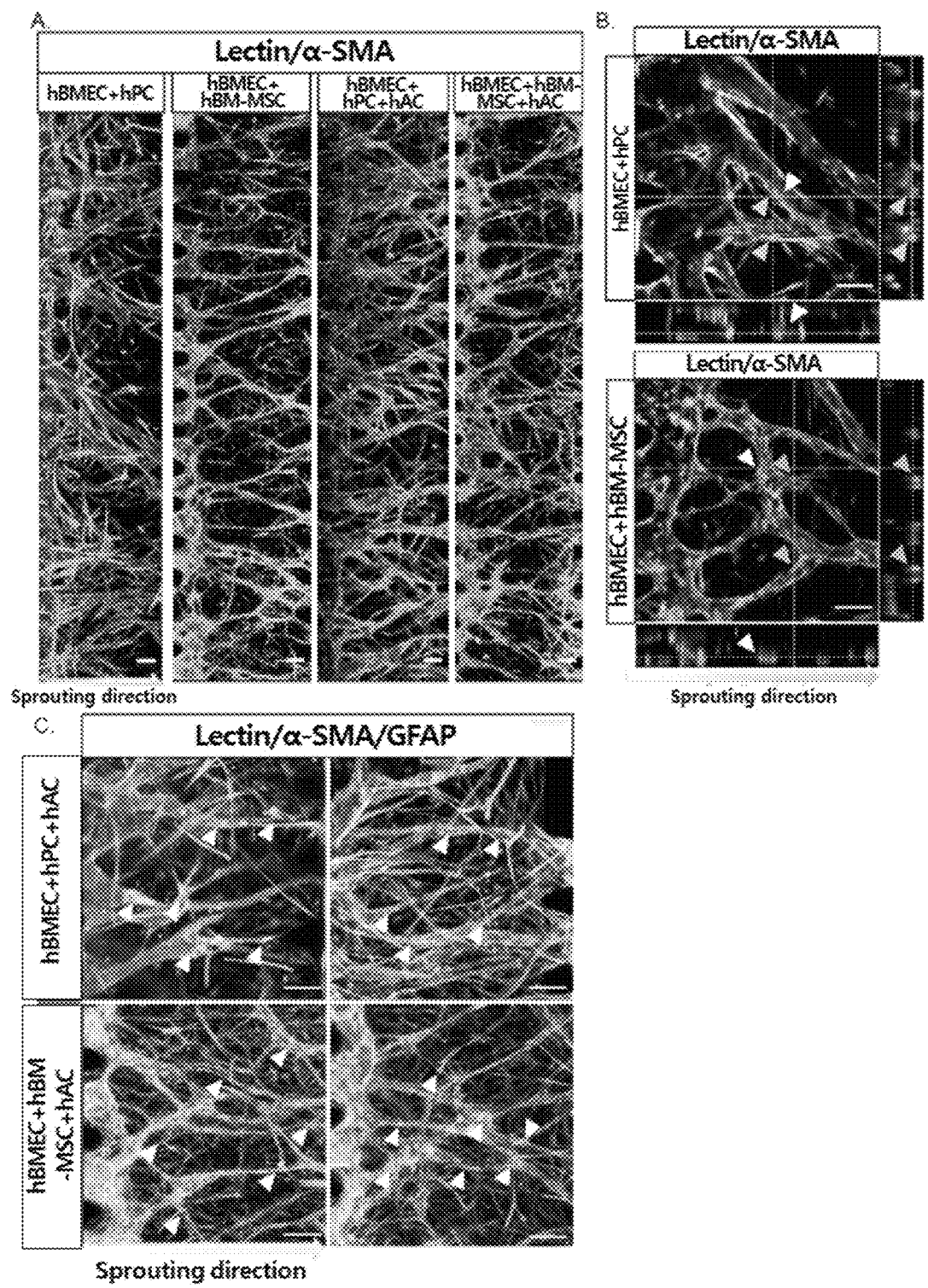

[FIG 3]
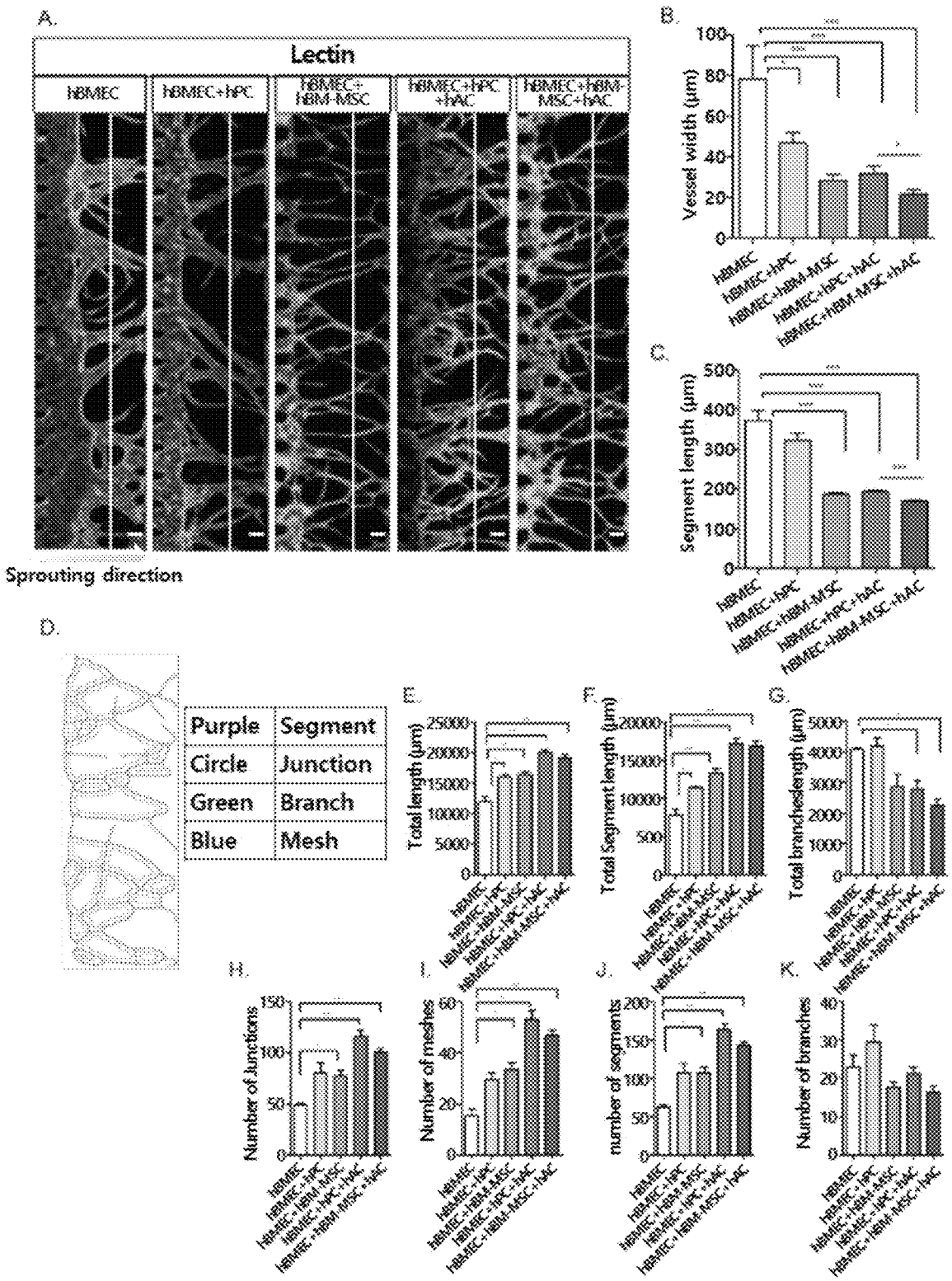

[FIG 4]
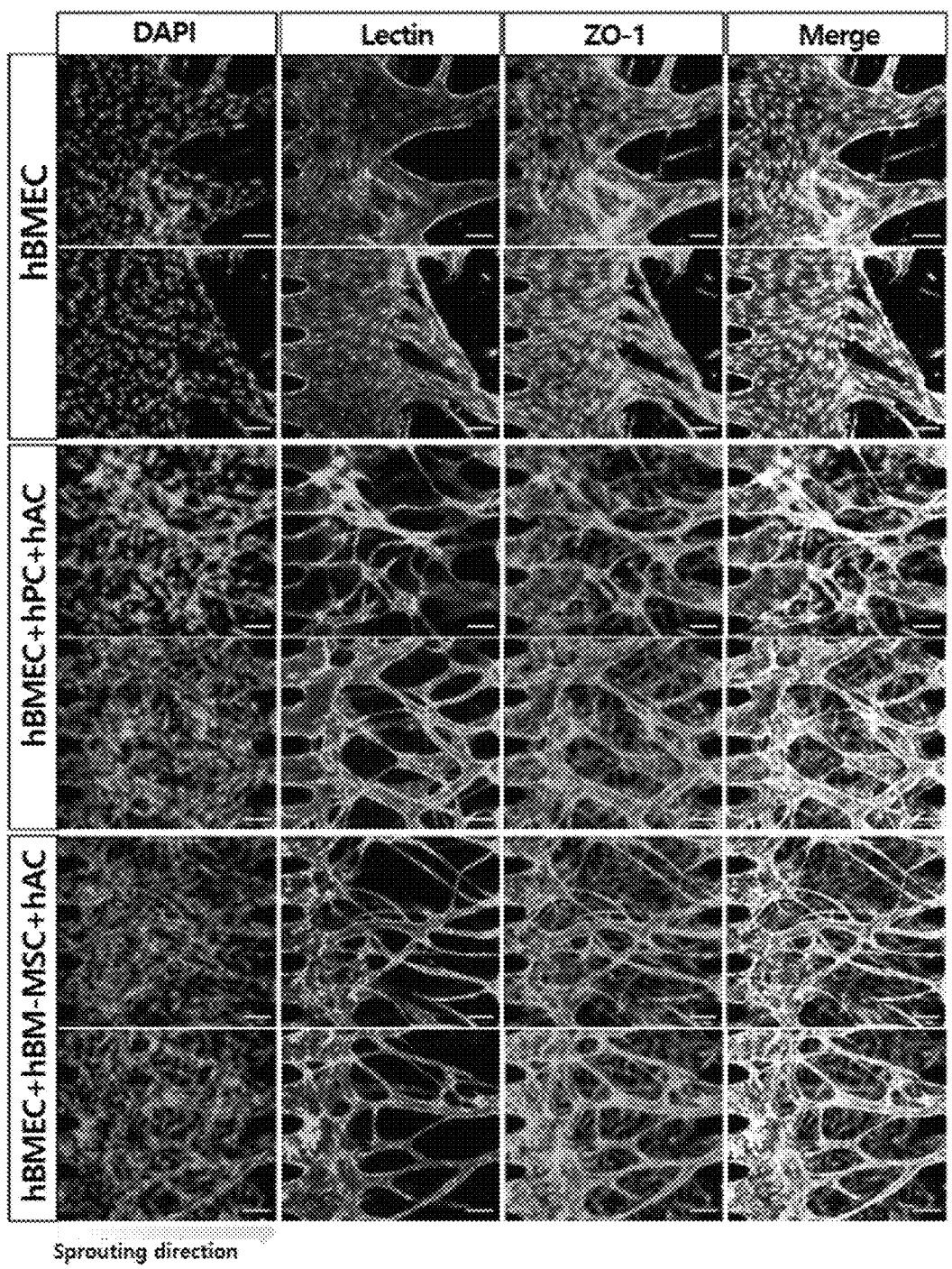

[FIG 5]
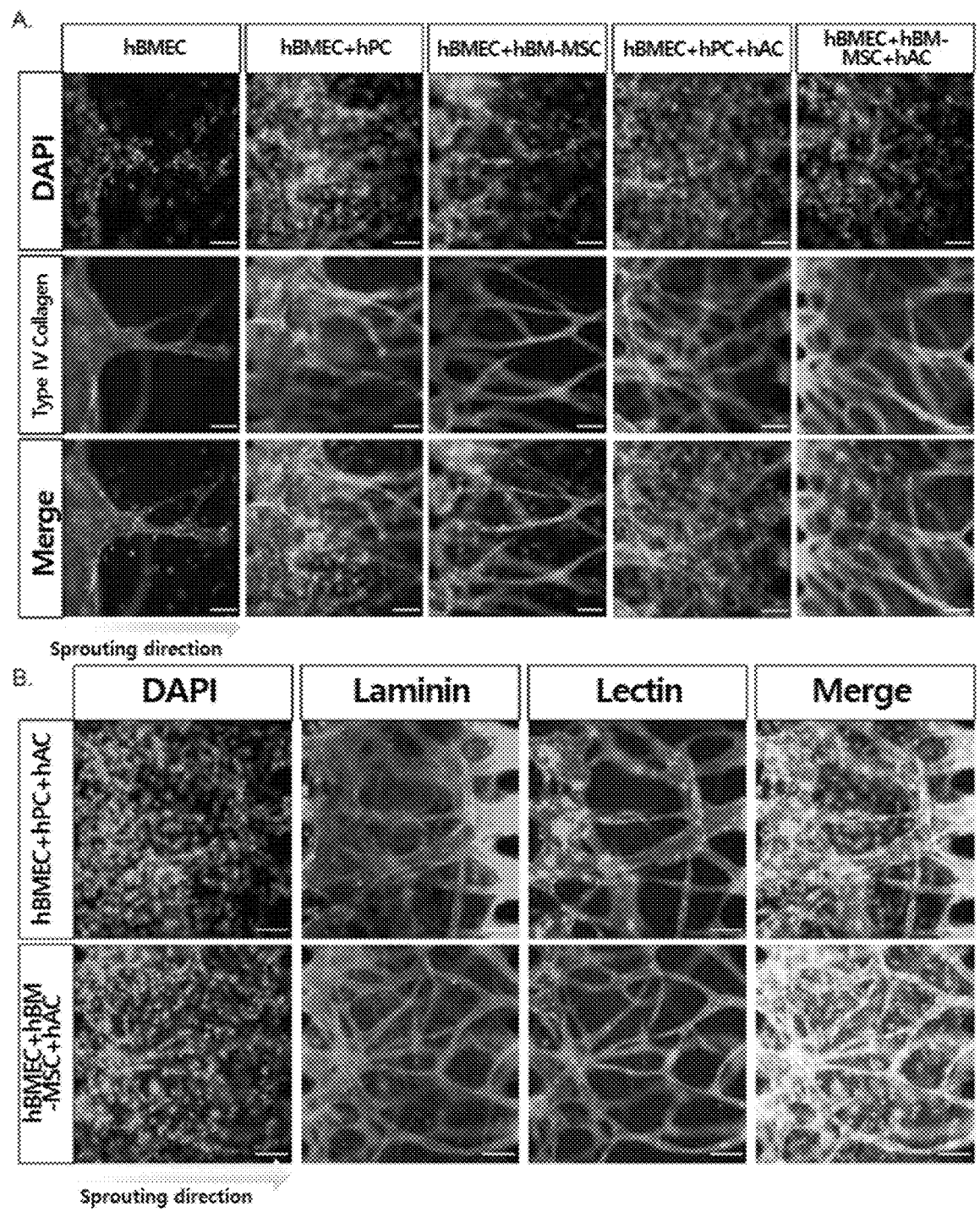

[FIG 6]
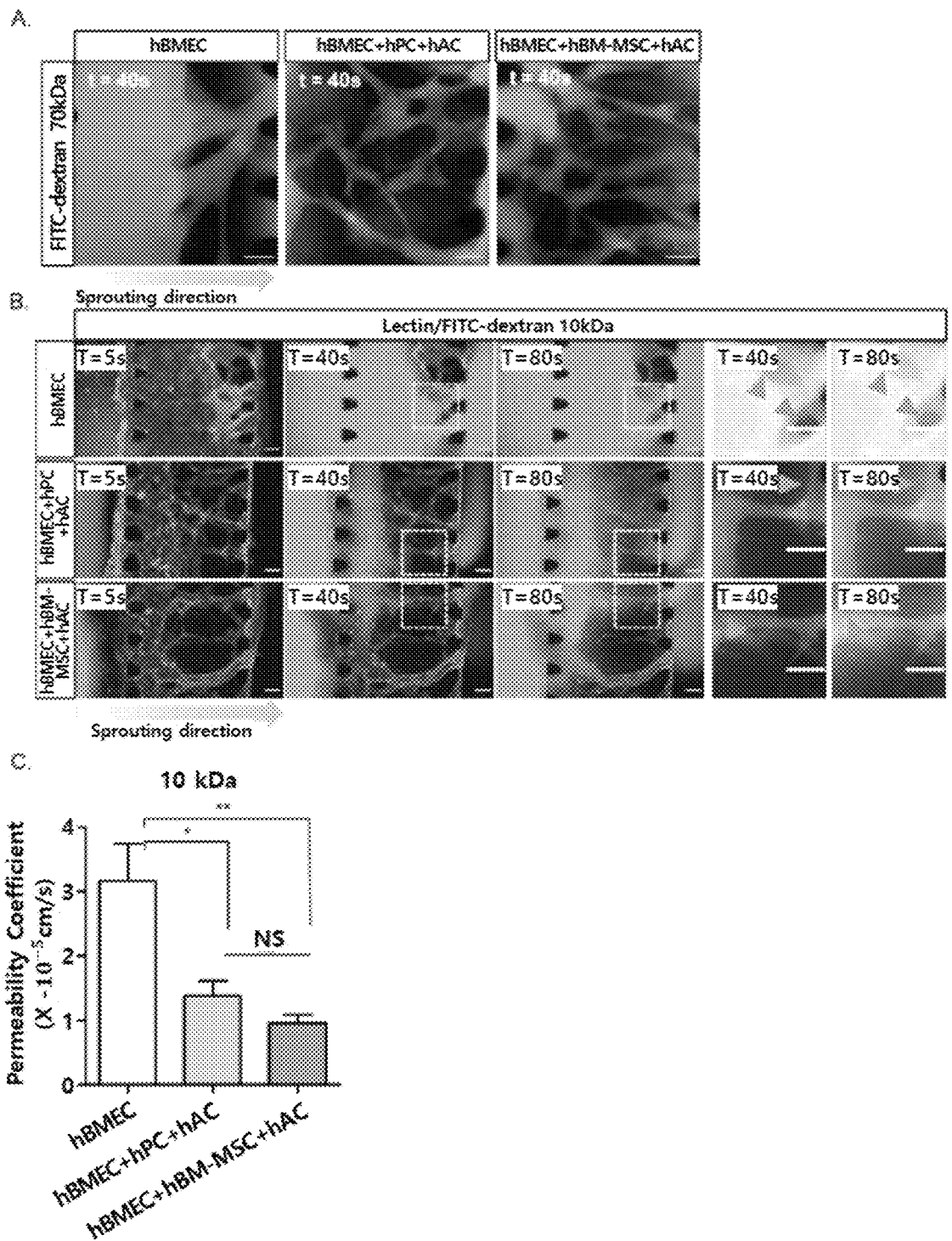

[FIG 7]
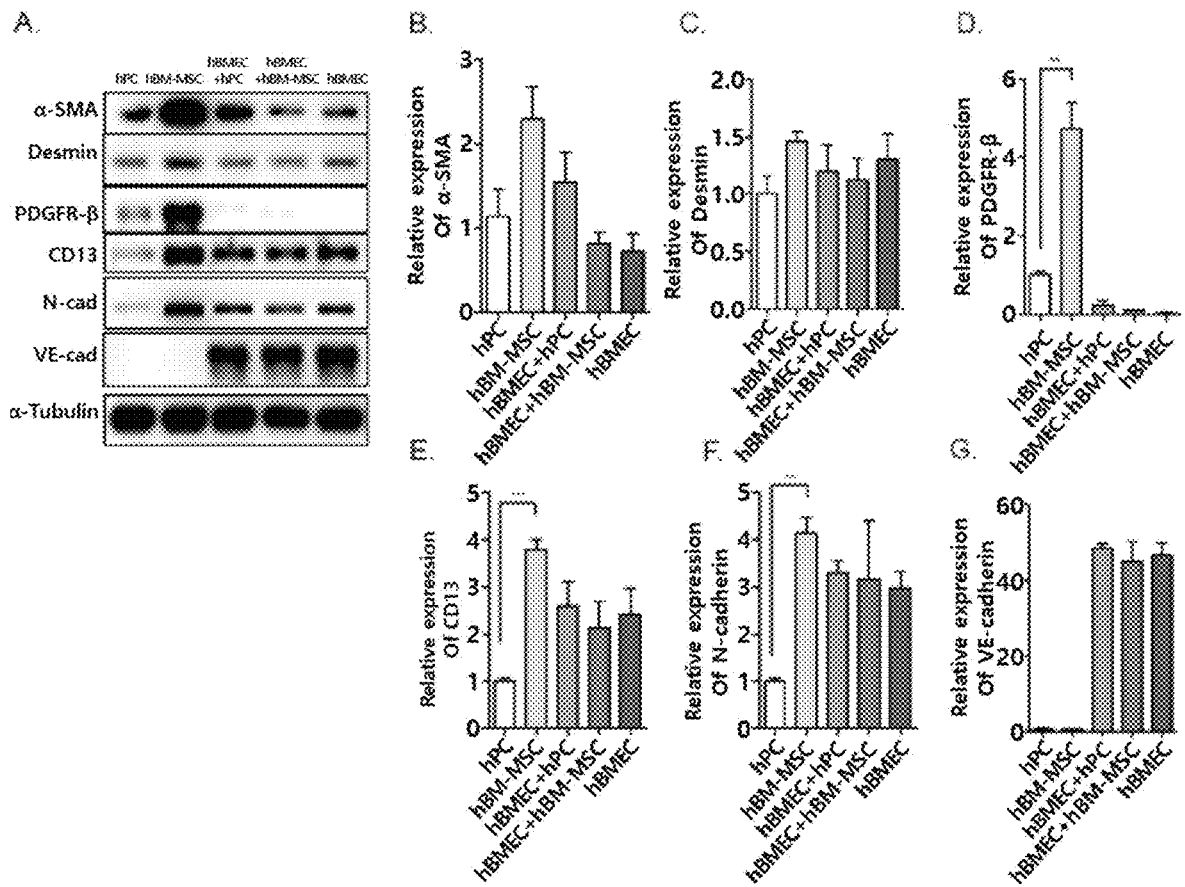

[FIG 8]
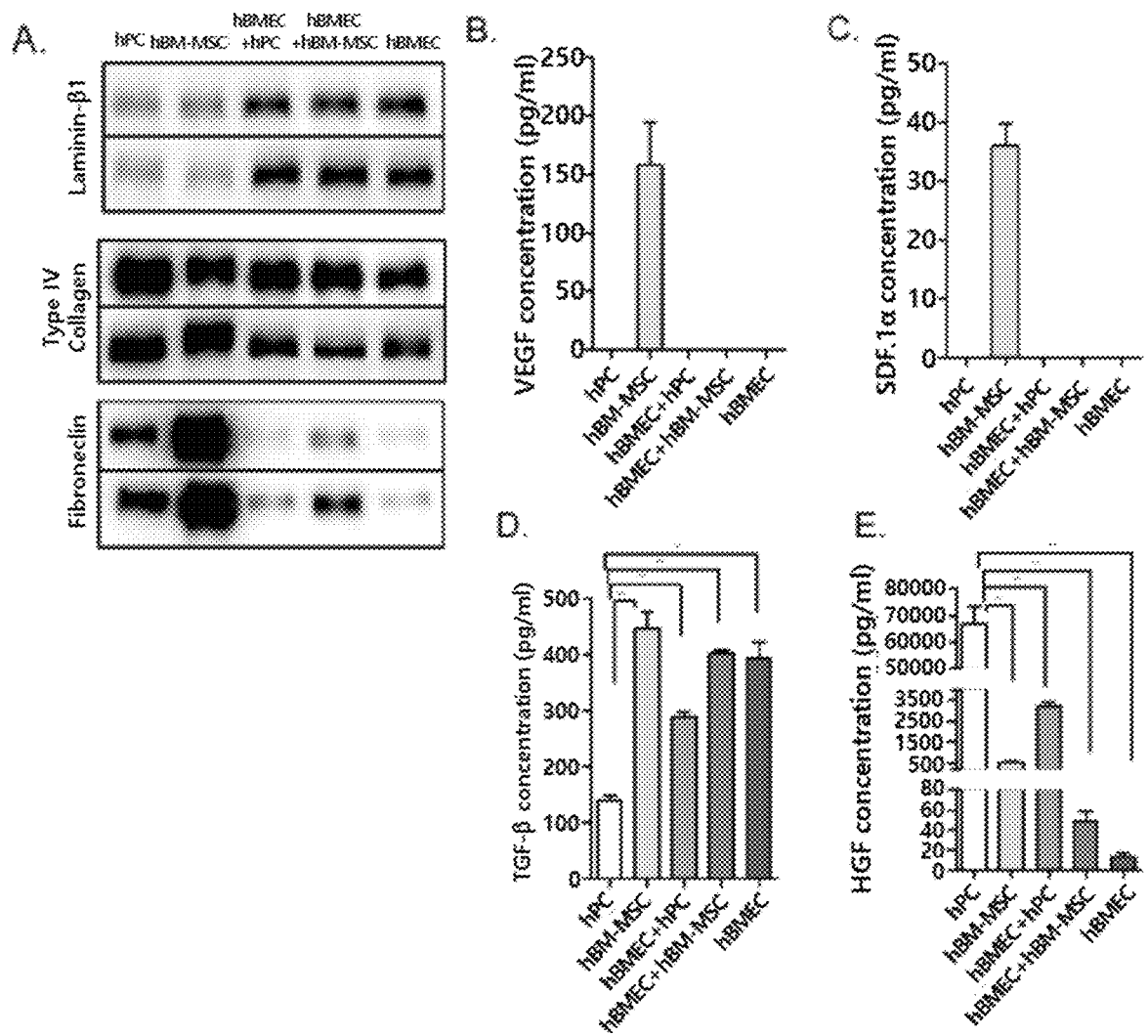

[ FIG 9 ]
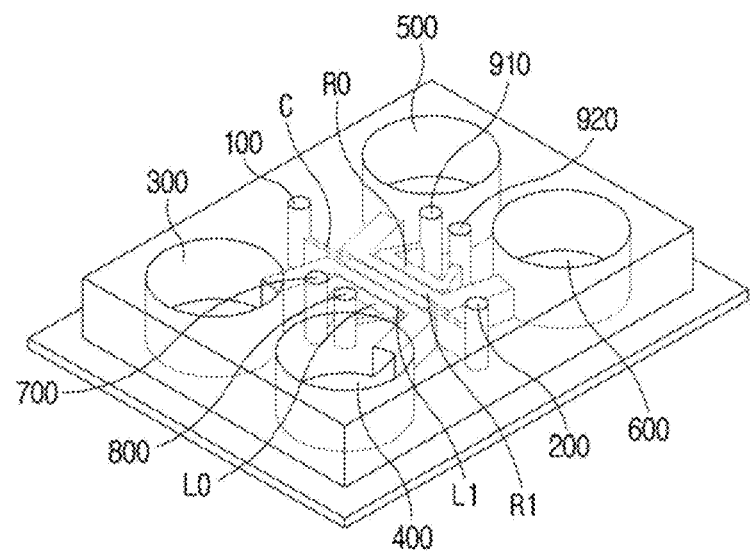
[ FIG 10 ]
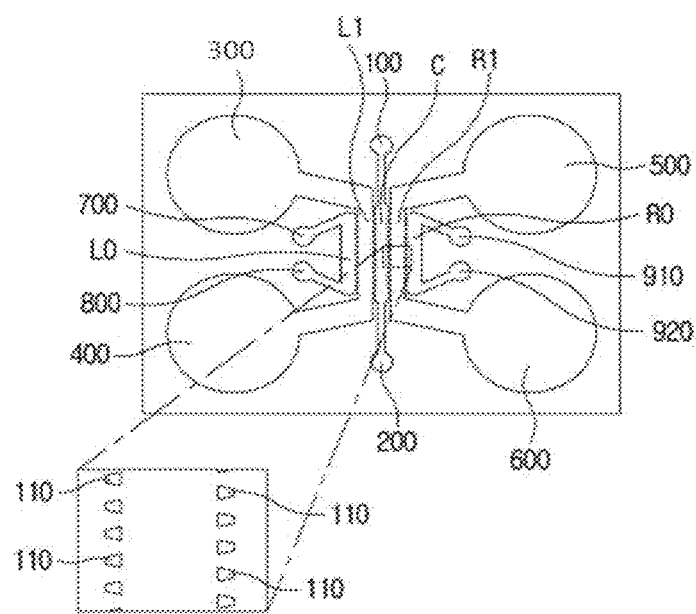

BLOOD BRAIN BARRIER-ON-A-CHIP

CROSS-REFERENCE TO RELATED APPLICATION

This non-provisional application claims priority to Korean Patent Application No. 10-2021-0036821 filed Mar. 22, 2021, the entire disclosure of which is incorporated herein by reference.

TECHNICAL FIELD

The present disclosure relates to a blood-brain barrier vascular network implemented in a microfluidic chip.

BACKGROUND

Despite a value of a two-dimensional (2D) cell culture model being recognized in medical life science research, the two-dimensional cell culture model may not explain the tissue-specific, differentiated functions of many cell types or may not accurately predict in vivo tissue function and drug activity because the cells are cultured in two dimensions on the bottom of the dish using a bacterial culture dish (petri dish) in the model. In particular, due to the limitation of the two-dimensional cell culture model, for brain tissue cells having neurons and neural stem cells in the three-dimensional contact in vivo, interest in a three-dimensional cell culture model that mimics well the spatial structure and biochemical complexity of living tissues is increasing. The three-dimensional cell culture model mimics the in vivo situation well, and may realize the directional growth and the complexity of cell-cell connection in in vitro experiments. In addition, the 3D cell culture model exhibits improved cell survival and enhanced neuronal differentiation compared to the 2D cell culture model. Therefore, the 3D cell culture model is useful to better capture the signaling pathways and drug responsiveness of various disease states compared to the 2D cell culture model in studying tissue functions on a molecular basis.

Recently, microfluidic technology which has been used not only throughout the field of biochemical research, but is also increasing in use in the neuroscience field is applied on a single chip or on a substrate to integrate the entire research process performed in the laboratory into a single chip. Microfluidic chips such as lab-on-a-chip incorporate complex components such as mixers, fluid separation channels and valves to integrate the various functions as required. Research on the microfluidic technology is gradually increasing in frequency of use thereof in cell-based research and other applied research. Microfluidic-based research has several advantages compared to conventional laboratory-level analysis processes because the former provides faster and more sensitive detection results while using a smaller volume of preparation.

The blood-brain barrier (BBB) is a vascular network that exists specifically in the capillaries of the brain. Damage to the normal blood-brain barrier occurs in various brain diseases such as ischemic vascular disease such as stroke, moyamoya disease, and Alzheimer's dementia. The technology to restore the blood-brain barrier in the early stage is a very important technology for the treatment and prophylactic treatment of these diseases. The blood-brain barrier has a three-layered structure having micro-vessels composed of vascular endothelial cells as the innermost portion, pericyte surrounding the micro-vessels, and the end-foot of astrocytes surrounding the pericyte. Under normal conditions, the BBB may act as a barrier that prevents many drugs and immune cells from being transferred to the brain matrix through the blood-brain barrier and thus performs the function of blocking/protecting the brain environment from changes in the blood. However, as in the case of the ischemic stroke, when a blood clot occurs and blocks the blood vessel, the blood-brain barrier and surrounding nerve cells are exposed to the ischemic state and thus the function of the blood-brain barrier is lost. Thus, various immune cells in the blood, especially inflammatory cells, penetrate into the brain matrix. This acts as the cause of various diseases. This causes damage to brain function, leading to various brain diseases. In this process, loss of function of pericyte is recognized as one of the very important initial reactions.

Further, stroke is the second leading cause of death worldwide. About 84% of these deaths are caused by ischemic stroke. In Korea, stroke is the second most frequent cause of death, next to the cancer, and is more common than heart disease. Well-known risk factors about the stroke include high blood pressure, diabetes, aging, smoking, hyperlipidemia, hyperhomocysteinemia, and thrombophilia of blood vessels. Several other conditions may cause ischemic stroke. The most common cause of the ischemic stroke is arterial occlusion in the head, which is mainly due to atherosclerosis, gradual cholesterol deposition or thrombosis. Vascular occlusion occurs mainly due to thrombosis (53%) or due to embolism (31%). Recently, various stem cell therapeutic agents have been attempted as such therapeutic agents for stroke (Sarmah, D. et al. Clin Pharmacol Ther. 103, 990-998 (2018); Boese, A C et al. Stem Cell Res Ther. 9, 154 (2018); Chen, S J et al. Stem Cells Dev. 19, 1757-1767 (2010)). In this connection, animal stroke models are technically difficult and require a lot of expensive medical tools as specially designed and take a lot of time and effort to evaluate the efficacy thereof. Thus, it is difficult to evaluate the effect of various stem cell therapeutic agents for stroke treatment by applying the animal stroke models to preclinical studies. Therefore, a laboratory system for reconstruction of a blood-brain barrier (BBB) similar to a brain microvasculature in vivo is essential to develop various stem cell therapeutic agents or drugs that work for the treatment of brain injuries and diseases.

SUMMARY

A purpose of the present disclosure is to provide an in vitro blood-brain bather (BBB)-on-a chip.

Further, a purpose of the present disclosure is to provide a manufacturing method of an in vitro blood-brain barrier (BBB)-on-a chip.

In addition, a purpose of the present disclosure is to provide a drug screening method using the in vitro blood-brain barrier (BBB)-on-a chip.

To solve the above purposes, the present disclosure provides an in vitro blood-brain barrier (BBB)-on-a chip.

Further, the present disclosure provides a method for manufacturing an in vitro blood-brain barrier (BBB)-on-a chip.

In addition, the present disclosure provides a drug screening method using an in vitro blood-brain barrier (BBB)-on-a chip.

The blood-brain barrier vascular network structure (BBB on a chip) (in vitro blood-brain barrier (BBB)-on-a chip) formed in a microfluidic chip manufactured by the manufacturing method of the in vitro blood-brain barrier (BBB)-on-a chip according to the present disclosure may reconstruct the blood-brain barrier in a real human body more similarly due to a specific cell configuration, compared to the conventional in vitro blood-brain barrier (BBB)-on-a chip, and thus may be used as a more accurate in vitro blood-brain barrier, and may be used for the development of various cellular therapeutic agents or drugs that work in the treatment of various brain diseases.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTIONS OF DRAWINGS

FIG. 1 is a diagram identifying reconstruction of human BBB-like microvasculature on an angiogenesis microfluidic chip and a role of each cell on a capillary network, using two-color live-cell imaging:
- A: Schematic diagram of angiogenesis microfluidic chip;
- B: Phase contrast microscopy image of angiogenesis across a channel C on 7 days after cell inoculation (Scale bar=100 μm); and
- C to E: two-color live-cell images of human BBB-like microvasculature reconstructed with different combinations of hBMECs (PKH-red) with hPCs (PKH-green), hBM-MSCs (PKH-green) or hACs (PKH-green) at the seventh day (arrow: co-localization of hBMECs and hPCs or hBM-MSCs; and circle: junction of microvasculature).

FIG. 2 is a diagram illustrating lumenized endothelial vessels, cellular phenotypes and the vascular incorporation of hPCs, hBM-MSCs and hACs in a reconstructed human BBB-like microvasculature on a chip:
- A: Full image of human BBB-like microvasculature in channel C after immunofluorescence staining of endothelial cells (UEA-lectin) and pericyte (α-SMA) (day 7);
- B: Confocal Z-section image of reconstructed human BBB-like microvasculature (yellow arrow: hPC or hBM-MSC expressing α-SMA); and
- C: 3-color confocal image of human BBB-like microvasculature on the chip (endothelial tubes: UEA-lectin staining (red), pericyte: α-SMA staining (green), astrocyte end-foot: GFAP (yellow)) (Scale bar=100 μm).

FIG. 3 is a diagram showing the result of quantitative analysis of the structural pattern and characteristics of human BBB-like microvasculature on a chip:
- A: full image of hBMEC-capillary network in human BBB-like microvasculature on a chip reconstructed under different cell combinations (white line: angiogenesis start point, Scale bar=100 μm);
- B and C: Quantitative analysis of vessel diameter and vessel segment length on day 7 (n=6);
- D: Analysis tree by NIH Image J angiogenesis analyzer (purple: segment, circle: junction; green: branch, blue: mesh);
- E: Total length
- F: Segment length;
- G: Branch length;
- H: Number of junctions;
- I: Number of meshes;
- J: Number of segments; and
- K: Number of branches.

FIG. 4 is a diagram showing the expression of the tight junction protein ZO-1 in human BBB-like microvasculature on a chip (Scale bar=100 μm):
- Red: ZO-1;
- Green: endothelial marker lectin; and
- Blue: nucleus.

FIG. 5 is a diagram identifying the reconstruction of the basement membrane in human BBB-like microvasculature:
- A and B Immunofluorescence staining of basement membrane-related protein of BBB-like microvasculature on a chip (type IV collagen and lectin: red, and laminin: green).

FIG. 6 is a diagram identifying the permeability of human BBB-like microvasculature on a chip:
- A: Flow image of 70 kDa FITC-dextran (40 sec);
- B: Time-lapse fluorescence flow images of 10 kDa FITC-dextran (5, 40 and 80 seconds) (arrows: microvasculature leakage point); and
- C: Permeability coefficient of each microvasculature (n=3).

FIG. 7 is a diagram comparing the function of pericyte and angiogenesis-related protein expression between hPC and hBM-MSCs under mono- or co-culture with hBMEC.
- A: Western blot analysis of α-SMA, desmin, PDGFR-β, CD13, N-cadherin and VE-cadherin (in hBMECs: hPCs or hBM-MSCs in a 6:1 ratio similar to that in cell culture on a chip);
- B: Relative expression of α-SMA;
- C: Relative expression of desmin;
- D: Relative expression of PDGFR-β;
- E: Relative expression of CD13;
- F: Relative expression of N-cadherin; and
- G: Relative expression of VE-cadherin.

FIG. 8 is a diagram comparing the basement membrane and the expression of angiogenesis factor-related protein between hPC and hBM-MSC culture mediums under mono- or co-culture with hBMEC:
- A: Western blot analysis of laminin-β1, type IV collagen and fibronectin;
- B: ELISA analysis result of VEGF;
- C: ELISA analysis result of SDF-1α;
- D: ELISA analysis result of TGF-β; and
- E: ELISA analysis result of HGF.

FIG. 9 is a perspective view of an in vitro blood-brain barrier (BBB)-on-a chip implemented based on the present disclosure.

FIG. 10 is a plan view of an in vitro blood-brain bather (BBB)-on-a chip implemented based on the present disclosure.

DETAILED DESCRIPTION

In the following detailed description, reference is made to the accompanying drawing, which forms a part hereof. The illustrative embodiments described in the detailed description, drawings, and claims are not meant to be limiting. Other embodiments may be utilized, and other changes may be made, without departing from the spirit or scope of the subject matter presented herein.

Hereinafter, the present disclosure will be described in detail based on an implementation of the present disclosure with reference to the accompanying drawings. However, the following implementation is presented as an example of the present disclosure. When it is determined that a detailed description of a well-known method or component known to those skilled in the art may unnecessarily obscure the gist of the present disclosure, the detailed description thereof may be omitted. The present disclosure may be variously modified and applied within the description of the claims to be described later and the equivalent scope as interpreted from therefrom.

Further, terms used herein are terms used to properly present a preferred example of the present disclosure, and may vary depending on the intention of users or operators, or customs in the field to which the present disclosure belongs. Therefore, definitions of these terms should be made based on the contents throughout the present specification.

The terminology used herein is for the purpose of describing particular embodiments only and is not intended to be limiting the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In addition, although preferred methods or samples are described in the present specification, those similar or equivalent are included in the scope of the present disclosure. The contents of all publications described by reference in this specification are incorporated into the present disclosure.

As shown in FIG. 9 and FIG. 10, the structure of the chip according to the present disclosure is as follows.

In one aspect, an in vitro blood-brain barrier (BBB)-on-a chip according to the present disclosure includes: a blood-vessel formation channel C having a blood-vessel formation channel inlet at one end thereof and a blood-vessel formation channel outlet at the other end thereof; a pair of first culture liquid sinks disposed on one side of the blood-vessel formation channel and connected to each other via a sink channel (LI), each first culture liquid sink having each predefined space; a pair of second culture liquid sinks disposed on the other side of the blood-vessel formation channel and connected to each other via a source channel (RI), each second culture liquid sink having each predefined space; a first culture channel (LO) contacting the sink channel and having a first culture channel inlet at one end thereof and a first culture channel outlet at the other end thereof; and a second culture channel (RO) being in contact with the source channel and having a second culture channel inlet at one end thereof and a second culture channel outlet at the other end thereof, in which at boundary locations between the first culture channel, the sink channel, the blood-vessel formation channel, the second culture channel, and the source channel, a plurality of microstructures are formed to define gaps therebetween in which biochemical substances received in the channels react with each other.

In one implementation, the medium may be added to the culture liquid sink, and a mixture of fibrin gel and feeder cells may be added to the first culture channel inlet or the second culture channel inlet, and a mixture of astrocyte and fibrin gel may be added to the blood-vessel formation channel inlet.

In one implementation, blood vessel formation may occur in the blood-vessel formation channel.

In one implementation, the plurality of the microstructures may be spaced from each other by 100 μm, and a size of each gap may be 100 μm.

In one implementation, a length of the channel may be 3000 to 5000 μm, and the channel may have a vertical dimension of 100 to 200 μm.

In one implementation, a width of each of the blood-vessel formation channel, the first culture channel and the second culture channel may be 700 to 900 μm, and a width of each of the sink channel and the source channel may be 600 to 700 μm.

In one implementation, the chip is an in vitro blood-brain barrier-on-a chip which contains human astrocytes (hACs) and fibrin gel in the blood-vessel formation channel, and contains a mixture of EGM-2 medium and AM medium in the sink channel, and contains human brain microvascular endothelial cells (hBMECs) and human bone marrow-derived mesenchymal stem cells (hBM-MSCs) on a wall of the sink channel on a side face of the blood-vessel formation channel, and contains human lung fibroblasts (hLFs) and fibrinogen in the second culture channel.

In one implementation, hLFs and fibrinogen may be contained in a ratio of 3:1 (w/w).

In one implementation, EGM-2 medium and AM medium may be contained in a ratio of 1:1 (v/v).

In one implementation, hBMEC and hBM-MSC may be contained in a ratio of 6:1 (w/w).

In one embodiment, the in vitro blood-brain bather (BBB) may contain, as pericyte, bone marrow-derived mesenchymal stem cells (hBM-MSCs), fat-derived mesenchymal stem cells, blood-derived mesenchymal stem cells, and umbilical cord blood-derived mesenchymal stem cells, more preferably contain hBM-MSCs, which is significantly superior to hPCs in basement membrane reconstruction and angiogenesis induction of human-BBB microvasculature.

In one implementation, a VEGF concentration gradient may be present from the first culture channel to the second culture channel.

In one implementation, angiogenesis sprouting may begin at the wall of the blood-vessel formation channel on a side face of the sink channel.

In one aspect, the present disclosure relates to a method for manufacturing an in vitro blood-brain barrier (BBB)-on-a chip, the method including 1) manufacturing a microfluidic chip including a blood-vessel formation channel C having a blood-vessel formation channel inlet at one end thereof and a blood-vessel formation channel outlet at the other end thereof; a pair of first culture liquid sinks disposed on one side of the blood-vessel formation channel and connected to each other via a sink channel (LI), each first culture liquid sink having each predefined space; a pair of second culture liquid sinks disposed on the other side of the blood-vessel formation channel and connected to each other via a source channel (RI), each second culture liquid sink having each predefined space; a first culture channel (LO) contacting the sink channel and having a first culture channel inlet at one end thereof and a first culture channel outlet at the other end thereof; and a second culture channel (RO) being in contact with the source channel and having a second culture channel inlet at one end thereof and a second culture channel outlet at the other end thereof, in which at boundary locations between the first culture channel, the sink channel, the blood-vessel formation channel, the second culture channel, and the source channel, a plurality of microstructures are formed to define gaps therebetween in which biochemical substances received in the channels react with each other;

2) injecting hLFs, fibrinogen and thrombin into the second culture channel;
3) filling the blood-vessel formation channel with a mixture of hACs and fibrin gel;
4) filling the culture liquid sink with a culture medium;
5) positioning the chip such that the sink channel faces upwardly and the source channel faces downwardly; and
6) injecting cell suspension of hBMEC and hBM-MSC into a sink channel inlet.

In one implementation, hBMEC and hBM-MSC may be contained in a ratio of 6:1 (w/w).

In one implementation, hBMEC and hBM-MSC may be apposed to the wall face of the sink channel on one side of the blood-vessel formation channel.

In one aspect, the present disclosure provides a drug screening method using an in vitro blood-brain barrier (BBB)-on-a chip, the method including applying a candidate drug substance on the in vitro blood-brain bather (BBB)-on-a chip according to the present disclosure.

In one implementation, the above screening method may include comparing a BBB of the in vitro blood-brain bather (BBB)-on-a chip on which the candidate drug substance is applied with a BBB (the blood-brain barrier) of the in vitro blood-brain barrier (BBB)-on-a chip on which the candidate drug substance is not applied.

In one implementation, the candidate drug substance may be a therapeutic agent candidate drug substance for Parkinson's disease, Alzheimer's dementia, Moyamoya disease or ischemic brain disease, and the ischemic brain disease may be a cerebral stroke or a cerebral infarction.

In one implementation, the candidate drug substance may be a cell therapeutic agent containing stem cells.

In one aspect, the present disclosure provides a method for evaluating a permeability of a drug into BBB, the method including applying the drug to the in vitro blood-brain bather (BBB)-on-a chip according to the present disclosure; and evaluating the permeability of the drug into the BBB.

In one aspect, the present disclosure relates to a method for evaluating a therapeutic agent for a stroke, the method including inducing a stroke in the in vitro blood-brain barrier (BBB)-on-a chip according to the present disclosure; applying stem cells or drug therapeutic agent candidate substances onto the chip, and quantifying recovery level of the BBB.

In one aspect, the present disclosure provides a method for evaluating regeneration effectiveness of the blood-brain barrier by a cell therapeutic agent, in which the method includes applying a candidate cell therapeutic agent onto the in vitro blood-brain barrier (BBB)-on-a chip according to the present disclosure.

In one implementation, the cell therapeutic agent may be a cell therapeutic agent for replacing brain microvascular endothelial cells (BMECs), bone marrow-derived mesenchymal stem cells (BM-MSCs), pericytes, or astrocytes.

In one implementation, the cell therapeutic agents for replacing BMEC may include bone marrow-derived endothelial progenitor cells (BM-EPCs), fat-derived endothelial progenitor cells, blood-derived endothelial progenitor cells, umbilical cord blood-derived endothelial progenitor cells, and iPS-derived endothelial progenitor cells, and/or trans-differentiated endothelial progenitor cells.

In one implementation, the cell therapeutic agent for replacing BM-MSCs or pericytes may include bone marrow-derived mesenchymal stem cells (MSCs), iPS-derived mesenchymal stem cells, fat-derived mesenchymal stem cells, and blood-derived mesenchymal stem cells, umbilical cord blood-derived mesenchymal stem cells, mesenchymal stem cell-like cells and/or other tissue-derived pericytes.

In one implementation, the cell therapeutic agent for replacing astrocytes may include astrocytes differentiated directly from adipocytes, and bone marrow cells, iPS-derived astrocytes, trans-differentiated astrocytes, and/or endogenous astrocytes.

In one implementation, the cell therapeutic agent may be a stem cell therapeutic agent, and the stem cell may be any one or more selected from the group consisting of embryonic stem cells, adult stem cells, induced pluripotent stem cells, embryonic germ cells, and embryonic tumor cells, but is not limited thereto. The adult stem cell may be any one or more selected from the group consisting of hematopoietic stem cells, neural stem cells, and mesenchymal stem cells, but is not limited thereto.

The hematopoietic stem cells may be isolated from the umbilical cord or bone marrow. The neural stem cells may be isolated from brain tissue and the mesenchymal stem cells may be extracted from bone marrow, adipose tissue, or umbilical cord, but are not limited thereto.

In the present disclosure, the term "cell therapeutic agent" refers to cells and tissues produced via separation, cultivation and special manipulation from a subject, and refers to a medicine used for treatment, diagnosis, and prevention purposes. These cells may be used to treat, diagnose and prevent diseases through a series of actions such as proliferating and screening live autologous, allogeneic or xenogeneic cells in vitro or changing the biological characteristics of cells via other methods in order to restore the function of cells or tissues.

In the present disclosure, the term "stem cells" refers to undifferentiated cells in the stage before differentiation into each cell constituting a tissue. The differentiation thereof into specific cells may proceed via a specific differentiation stimulus (environment).

In the present disclosure, the term "mesenchymal stem cells (MSCs)" is also referred to as mesenchymal stem cells or adult stem cells, and collectively refers to stem cells isolated and cultured from tissues other than embryos. Mesenchymal stem cells are present in small amounts in most tissues that have already been differentiated, and their existence has been identified in almost all tissues as studied, such as umbilical cord blood, umbilical cord, teeth, eyes, placenta, hair follicles, lungs, and liver.

In one aspect, the present disclosure relates to a method for evaluating the regeneration effectiveness of the blood-brain barrier by candidate cells, the method including injecting the candidate cells capable of replacing astrocytes into the blood-vessel formation channel inlet of the in vitro blood-brain barrier (BBB)-on-a chip according to the present disclosure; and injecting the candidate cells capable of replacing any one or more cells selected from the group consisting of brain microvascular endothelial cells (BMECs), pericytes, and bone marrow-derived mesenchymal stem cells (BM-MSCs) into a wall of the sink channel on one side of the blood-vessel formation channel of the chip.

In one implementation, the method may further include any one or more steps selected from the group consisting of:
1) identifying a diameter and a web-like structure of an endothelial microvasculature in order to identify the reconstruction of the endothelial microvasculature of the blood-brain barrier (BBB)-on-a chip;
2) identifying lumenized endothelial vessels, phenotype of the candidate cells, and vascular incorporation of the candidate cells in the microvasculature of the blood-brain barrier (BBB)-on-a chip;
3) identifying the diameter, the total length, the length of the segment, the length of the branch, the number of junctions, the number of meshes, the number of segments, and the number of branches of the blood vessel of the microvasculature of the blood-brain barrier (BBB)-on-a chip;
4) identifying a tight junction in the microvasculature of the blood-brain bather (BBB)-on-a chip;
5) identifying the permeability of the microvasculature of the blood-brain barrier (BBB)-on-a chip; and
6) identifying the expression level of a basement membrane reconstruction-related protein or angiogenesis-related protein of the candidate cells capable of replacing the microvascular endothelial cell, pericyte or BM-MSC.

In one implementation, the basement membrane reconstruction-related protein or angiogenesis-related protein of step 6) may include any one or more selected from the group consisting of α-SMA, desmin, PDGFR-β, CD13, N-cadherin, VE-cadherin, laminin-β1, type IV collagen, fibronectin, VEGF, SDF-11α, TGF-β, and HGF.

The present disclosure will be described in more detail through the following examples. However, the following examples are only for specifying the contents of the present disclosure, and the present disclosure is not limited thereto.

Example 1. Fabrication of BBB-Like Microvasculature Using Angiogenesis Microfluidic Chip 1-1. Manufacturing of Microfluidic Device The microfluidic device was fabricated by soft lithography and replica molding method. Specifically, a master for molding was prepared by a photolithography process of patterning microstructures on a silicon wafer using photoresist SU-8 (MicroChem, Newton, MA, USA). A PDMS (polydimethylsiloxane) (Sylgard 184, Dow Corning, Midland, MI, USA) prepolymer was prepared by mixing a 10:1 (w/w) PDMS base and a curing agent with each other. The mixture was heat cured on a 90° C. hot plate for 30 minutes and cast into the pattern of the master. We separated the cured PDMS piece from the master. An injection hole and a medium storage were punched using a sample punch. The PDMS piece was washed with a residue-free tape and treated with a cover glass and oxygen plasma. After the plasma treatment, the PDMS piece was bonded to a glass coverslip to form a covalent bond. A resulting device was dried at 70° C. for 2 days to restore the hydrophobicity required for patterning the hydrogel on the microchannel. Before loading the cells thereon, the chip was sterilized by exposing the chip to UV for 20 minutes. The microfluidic device was composed of five channels: left outer (LO), left inner (LI), center (C), right inner (RI), and right outer (RO). The LO and RO channels of the microfluidic chip or device were channels to be inoculated (dispensed) with a mixture of fibrin gel and feeder cells for secreting VEGF for blood vessel formation. The LI and RI channels are medium channels, and the top and bottom of the channels are connected to the storage. The channel C is the main channel in which blood vessel formation occurs. There are 4 storages in one microfluidic device. The top of the storage is opened so that medium may be replenished therein. Each of all channels is 3700 μm long and 150 μm high. Further, the width of each of the channels C, RO and LO is 800 μm, and the width of each of LI and RI is 650 μm. In addition, posts with 100 μm pores are spaced from each other by 100 μm, and are arranged in the boundary region between the channels C, RO and LO to separate the channels from each other.

1-2. Fabrication of Microfluidic Angiogenesis Model

A microfluidic blood vessel model in which human BBB-like microvasculature was formed was produced on the chip by applying different cell components, in various combinations, into the device manufactured in Example 1-1 (FIG. 1A). The model was identified via visualization using two colors fluorescence live-cell imaging. Specifically, bovine plasma-derived fibrinogen (10 mg/ml, Sigma Aldrich) was diluted in DPBS (Dulbecco's phosphate-buffered saline) (Welgene) and was mixed with aprotinin (4 KIU/ml, Sigma Aldrich) in a ratio of 25:4. To establish a gradient of VEGF concentration across the microfluidic device, human lung fibroblasts (hLFs) (final cell density: $6×10^6$ cells/ml) were mixed with fibrinogen at a ratio of 3:1 and then thrombin (Sigma Aldrich) was rapidly added thereto at a ratio of 50:1 just before injection into the RO channel so that the final concentration was 1 U/ml, thereby preparing a fibrin gel within 3 minutes. To simulate the brain parenchyma for BBB-like microvasculature, the channel C was filled with a mixture of human astrocytes (hACs) (final cell density: $4.5×10^6$ cells/ml) and fibrin gel. In order to observe the growth pattern of BBB-like microvasculature in the microfluidic device, the cells were labeled with PKH green and/or PKH red (Sigma Aldrich) before inoculation. After the cell inoculation, the two upper storages were filled with a 1:1 ratio of EGM-2 and AM medium mixture, and the two lower storages were gently aspirated to wet the hydrophobic medium channel. Then, the four storages were filled with medium and incubated at 37° C. One day later, after removing the culture medium from the four storages, the device was tilted vertically so that the LI channel faced upwards and the RI channel faced downwards. For directional angiogenesis according to the VEGF concentration gradient through the brain parenchyma-mimicking channel C, we injected 5 μl of the cell suspension (final cell density $5×10^6$ cells/ml) of hBMEC, hBMEC+hPC (6:1) and hBMEC+hBM-MSC (6:1) into one of the storages connected to the channel LI (The BBB of a normal brain is composed of endothelial cells and pericytes in a ratio of about 3:1. In this microfluidic angiogenesis model, hPCs and hBM-MSCs have higher cell proliferation and matrix-degrading capacity, so the ratio is reduced to 6:1), and the cells were incubated for 30 minutes at 37° C., such that the cells were apposed to a post on the left side of the channel C. After the cell apposition, the four storages were filled with 130 μl of culture medium. To create a spontaneous medium flow inside the microfluidic device, 10 μl of medium was added to two storages connected to the RI channel. Thereafter, for in vitro BBB-angiogenesis, the microfluidic device was incubated for 7 days under 37° C. and 5% $CO_2$ condition, and the culture medium was changed every 2 days. Thus, human BBB-like microvasculature having different cellular configurations was established.

Example 2. Establishment and Identification of Microfluidic Angiogenesis Model on in Microfluidic Chip 2-1. Cell Migration Identification The kinetic of the tip cell migration and microvasculature architecture was observed for 7 days by phase-contrast microscopy. The tip cells were sprouted from the initial cell inoculation to the channel C toward the VEGF gradient in all five groups. However, its migration was much faster in the hBMEC+hBM-MSC group than that in the hBMEC only or hBMEC+hPC group at day 3, whose migration seems to pass through entire channel C at day 5 and the maturation and remodeling of microvasculature seem to proceed at day 7 (FIG. 1B). This result suggests that hBM-MSCs may function better in the formation of the tip cells and migration of endothelial cells than hPCs.

2-2. Identification of Acting as a Pericyte

In order to identify the role of hBM-MSCs in the reconstruction of endothelial microvasculature, we observed the growth pattern of BBB-like microvasculature by visualizing via PKH green or PKH red live-cell labeling and imaging. Thus, both PKH green-labeled hPCs and PKH green-labeled hBM-MSCs were nicely co-localized on the PKH red-labeled hBMECs microvasculature on day 7, whose incorporation made the endothelial microvasculature get much smaller in diameter and more abundant in the capillary web-like structure (FIG. 1C). Especially, most PKH green-labeled hBM-MSCs were very closely apposed on the PKH red-labeled hBMECs in the microvasculature, which was more abundant than that of hPCs. Thus, this result confirms that hBM-MSCs can work as a pericyte on the hBMEC microvasculature even more efficiently than hPCs, whose function is independent of the presence of hPCs.

2-3. Cell Component Tracking

To track individual cellular components on the hBMEC-microvasculature, hBMECs were labeled with PKH red and hPCs, hBM-MSCs and hACs were labeled with PKH green to observe a microfluidic angiogenesis model. Thus, the incorporation of hACs in the microfluidic angiogenesis model made the hBMEC-microvasculature smaller in diameter and increased the capillary web-like structure (FIG. 1D and FIG. 1E). Especially, the reduction of the vessel diameter was more prominent in hBM-MSCs-incorporated BBB-like microvasculature than that in hPCs-incorporated BBB-like microvasculature. In the visualization of PKH green-labeled hACs in the BBB-like microvasculature, most hACs were present as impregnated within the gel, but some were stretched toward microvasculature, suggesting astrocyte end-foot projection to the BBB-microvasculature. Also, the number of vessel junctions seems to increase with the incorporation of hACs.

Taken together, human BBB-like microvasculature was successfully reconstructed on the microfluidic chip, and this system is suitable to estimate the role of candidate cell therapeutics as vascular pericyte in the BBB reconstruction such as hBM-MSCs as well as the contribution of other cellular components on the establishment of BBB architecture in vitro.

Example 3. Identification of Interaction Between hBM-MSCs as Pericyte and Astrocyte End-Foot in BBB-Like Microvasculature on Chip To identify the cell phenotypes within the BBB-like microvasculature structure, endothelial tubes were stained with lectins, pericyte with $\alpha$-SMA and astrocyte end-foot with GFAP. Specifically, 30 µl of 3.7% formaldehyde (Sigma Aldrich) was added to the upper two storages to fix the BBB-like microvasculature in the microfluidic device prepared in the Example for 15 minutes. Then, the sample was treated with 0.2% Triton X-100 (Sigma Aldrich) (in PBS) for 20 minutes to achieve permeability, and the sample was treated with 3% FBS (Sigma Aldrich) (in PBS) for 1 hour to block non-specific binding. For endothelial staining, dylight 594 (Vector, Burlingame, CA, USA, 1:200) or Fluorescein (Vector, 1:200)-conjugated lectin was applied thereto. The nuclei were stained with DAPI (Sigma Aldrich, 1:500) at 37° C. for 1 hour. All reagents for the staining procedure were added to the upper two storages. After staining, the four storages were filled with PBS during imaging to prevent drying of the medium channel. Further, for immunofluorescence staining, the sample was treated with aSMA (Dako, Santa Clara, CA, 1:100) and GFAP (Abcam, Cambridge, MA, USA, 1:500) as primary antibodies at 4° C. for 2 days. The sample was treated with each of secondary antibodies goat anti-mouse Alexa 488 (Invitrogen, Waltham, MA, USA, 1:500), goat anti-rabbit Alexa 488 (Invitrogen, 1:500), goat anti-mouse Alexa 546 (Invitrogen, 1:500) and goat anti-rabbit Alexa 647 (Invitrogen, 1:500) overnight at 4° C.

As a result of observation at low magnification, the overall appearance of the lectin-positive endothelial capillary-like network and $\alpha$-SMA-positive pericyte apposition were observed. Similar to what was observed in the PKH-labeled microvasculature, hBM-MSCs incorporation decreased the blood vessel diameter and increased blood vessel density and network formation. This was significantly more efficient than hPCs regardless of the presence of hACs (FIG. 2A). As a result of observation at high magnification, lumenized hBMEC blood vessels were clearly detected, and close apposition of $\alpha$-SMA-positive pericyte on the abluminal surface of endothelial vessels was found in both hPCs and hBM-MSCs-incorporated microvasculatures via confocal Z-section imaging (FIG. 2B). Further, the addition of hBM-MSCs resulted in a smaller blood vessel diameter and higher capillary density of hBMEC-microvasculature than hPCs. In addition, GFAP-positive-ramified astrocyte end-foot projections and their close apposition to blood vessels were also detected in hPCs or hBM-MSCs-incorporated microvasculature (FIG. 2C). Therefore, hBM-MSCs may be incorporated into a BBB-like microvasculature as an endothelial-encircling pericyte expressing $\alpha$-SMA. It may be identified that this further affects the structure of the BBB-like microvasculature, which is similar to the BBB in vivo.

Example 4. Quantitative Analysis of Structure Characteristics of BBB-Like microvasculature reconstructed on microfluidic chip Capillary fine web-like structure is very important to effectively supply sufficient oxygen and nutrients to tissues. To quantitatively analyze the blood vessel diameter of the BBB-like microvasculature on the microfluidic chip according to the present disclosure, on the 7th day, the luminal portion of the endothelial microvasculature was stained with a lectin. Based on the confocal images of 5 groups (hBMEC, hBMEC+hPC, hBMEC+hBM-MSC, hBMEC+hPC+hAC and hBMEC+hBM-MSC+hAC groups), the blood vessel width at a ⅔ point from the angiogenesis initiation point was measured (the diameter of the human brain capillaries is about 5 to 10 µm) (FIG. 3A). Leica DMI 4000 B fluorescence microscope (Leica Microsystems, Wetzlar, Germany) and Nikon Ti2-E-inverted microscope (Nikon, Tokyo, Japan) were used for microvasculature imaging. Confocal images were analyzed with Fiji software. In this connection, since the entire stack of the Z-section image contains at least two blood vessels at the same time, the Z-section image was divided into two parts based on the blood vessel network pattern, which was stacked into a 2D image. To identify other variables for microvascular structure that are important for estimating the architectural quality of the in vitro-reconstructed microvasculature and similarity thereof with in vivo BBB, the length of the segment (a blood vessel separated by two vascular junctions at both ends) considered as an important variable for estimating the microweb-like capillary network and blood vessel density was identified. Segment length was analyzed with NIH Image J software. The total length, segment length, branch length, and the numbers of meshes, segments and junctions as analyzed by angiogenesis analyzer were analyzed with image J software.

As a result, blood vessel width was 78.63±16.13 μm in hBMEC alone group, 46.77±5.05 μm in hBMEC+hPC group, 28.2±2.99 μm in hBMEC+hBM-MSC group, 31.71±3.78 μm in hBMEC+hPC+hAC group, and 21.58±2.11 μm in the hBMEC+hBM-MSC+hAC group (FIG. 3B). hBM-MSCs were found to be remarkably effective in vasoconstriction compared to hPCs. Astrocytes have also been shown to contribute to thinning of blood vessels to some extent. Its effect was better observed in the microvasculature of the hBMEC+hPC+hAC group. Further, multiple short segments may form finer networks and higher vascular density in the microvasculature. As a result of analyzing and identifying this with an angiogenesis analyzer, the mean segment lengths in the vascular network in the respective groups were as follows: 374.1±25.28 μm in the hBMEC group, 322.1±20.1 μm in the hBMEC+hPC group, 187.6±4.26 μm in the hBMEC+hBM-MSC group, and 193.2±4.86 μm in the hBMEC+hPC+hAC group, and 169.5±3.735 μm in the hBMEC+hBM-MSC+hAC group (FIGS. 3C and 3D, Table S1, and Supplementary FIG. 1). In particular, hBMEC-microvasculature showed the most dramatic decrease in segment length due to incorporation of hBM-MSCs (374.1±25.28 μm to 187.6±4.26 μm). Further, astrocyte was able to further reduce segment length. This effect was more pronounced in hPCs-incorporated microvasculature (193.2±4.86 μm to 322.1±20.1 μm) than hBM-MSCs-incorporated microvasculature (169.5±3.735 μm to 187.6±4.26 μm), and was more similar to that observed in BBB in vivo. Further, the total blood vessel length (FIG. 3E), the total segment length (FIG. 3F), the number of junctions (FIG. 3H), the number of meshes (FIG. 3I) and the number of segments (FIG. 3J) that have a positive correlation with the architectural maturity of the fine web-like network, and the total branch length (FIG. 3G) and the number of branches (FIG. 3K) related to the immature vascular network were measured. As a result, the BBB-like microvasculature reconstructed with each of hBMEC+hPC+hAC and hBMEC+hBM-MSC+hAC had a larger number of segments, meshes, and junctions, compared to the BBB-like microvasculature reconstructed with each of hBMEC alone, hBMEC+hPC and hBMEC+hBM-MSC. The former had a smaller number of branches, compared to the latter. These architectural characteristics showed no significant difference between hPCs and hBM-MSCs, indicating that astrocytes play the most important role in maturation of fine web-like capillary networks. Further, a longer branch length (FIG. 3G) and a larger number of branches (FIG. 3K) were observed in the hBMEC+hPC group compared to the hBMEC+hBM-MSC group. However, when adding hACs to hPCs-incorporated hBMEC-microvasculature, the branch length and number of branches could be significantly reduced. Thus, it could be inferred that hACs may play a more important role in the maturation of the microvasculature.

Example 5. Identification of Role of hPCs and hBM-MSCs as Pericyte in Microfluidic BBB-Like Microvasculature 5-1. Identification of Tight Junctions To identify the formation of tight junctions between endothelial cells as one of the specific phenotypic characteristics of BBB, using the anti-ZO-1 antibody conjugated with Alexa 594 (Invitrogen, 1:100) as a primary antibody, immunofluorescence staining analysis as in Example 3 was performed to identify the expression of the tight junction protein ZO-1 in microvasculatures of chips using hBMEC alone group, hBMEC+hPC+hAC group, and hBMEC+hBM-MSC+hAC group, respectively, on day 7. As a result, in the hBMEC alone group, ZO-1 expression was mainly not localized at the cell boundary and diffused into the cytoplasm which was not present in a tubular structure. On the other hand, in the hBMEC+hPC+hAC group and the hBMEC+hBM-MSC+hAC group, ZO-1 expression was localized only at the cell boundary, resulting in tight junction lining between adjacent endothelial cells (FIG. 4).

5-2. Identification of Maturity of BBB-Like Microvasculature

In the brain BBB, the abluminal portion of the endothelial tubes and the microvascular pericyte are tightly surrounded with the endothelial basement membrane. Thus, in order to identify the continuous coverage of the basement membrane along the BBB-like microvasculature as an important criterion for estimating the maturity of the BBB microvasculature, the expression of type IV collagen and laminin, as the main components of the basement membrane, was visualized via immunofluorescence staining. Specifically, type IV collagen (Dako, 1:100) and laminin (Dako, 1:100) were used as primary antibodies to perform immunofluorescence staining analysis as in Example 3.

As a result, only in the case of microvasculatures made with hBMEC, type IV collagen was not discretely localized on the abluminal surface of the microvasculature. On the other hand, when capillary web-like microvasculature was identified, type IV collagen was discretely detected along the microvasculature in all four groups into which hPCs or hBM-MSCs were incorporated, but was not discretely detected in pericyte or astrocyte into which hPCs or hBM-MSCs were not incorporated (FIG. 5A). Further, the discrete localization of laminin on the abluminal portion was also noted in the BBB-like microvasculature of hBMEC+hPC+hAC and hBMEC+hBM-MSC+hAC. The laminin was also co-localized only onto lectin-positive microvasculature (FIG. 5B). Thus, both hPCs and hBM-MSCs injected into the microfluidic BBB-like microvasculature were found to restore tight junctions and reformation of the abluminal membrane along the microvasculature to play a role as a BBB pericyte in the maturation of the BBB structure.

Example 6. Identification of Perfusion of Blood Vessel of BBB-Like Microvasculature on Chip As albumin in the blood diffuses into the brain parenchyma upon BBB collapse, the leakage of albumin from the BBB in vivo is identified in various preclinical studies.

Therefore, to realize such BBB-like microvasculature perfusion, two sizes of FITC-dextran (10 kDa and 70 kDa FITC-dextran) (Sigma Aldrich) were applied to the channel LI and the time-lapse imaging was recorded. Thus, permeability through the blood vessel of BBB-like microvasculature in the microfluidic device was visualized. Specifically, the endothelial lumen of the BBB-like microvasculature was visualized via live-staining for 30 minutes with lectin to which dylight 594 (Vector, 1:200) was conjugated. After filling all the storage with PBS, 5 μl of FITC-dextran was added to the upper storage connected to the channel LI. Images were captured every 5 seconds for 80 seconds under a fluorescence microscope. The permeability coefficient was calculated according to Equation 1 below:

$$p = \frac{1}{L_w} \times \frac{dI/dt}{I_v}$$ [Equation 1]

[$L_w$: The length of the blood vessel wall separating the perivascular region and the microvascular region from each other; $I_v$: Average strength of the interior of the microvasculature; and I: Total strength of the perivascular area.]

As a result, it was identified that 70 kDa FITC-dextran which has a molecular size similar to that of albumin passes through channel C in microvasculatures in all of the groups, thereby forming a vascular network capable of continuous perfusion (FIG. 6F). Thus, in order to compare the permeable barrier functions of microvasculatures in the several groups with each other, hBMEC-microvasculatures were visualized by live-cell imaging via fluorescent lectin staining, and as a result, it was identified that 10 kDa FITC-dextran flows into the channel LI. From the results identified by over-time imaging, FITC-dextran entered the microvasculature of the channel C within 5 seconds. 10 KDa FITC-dextran was observed at 40 seconds in the hBMEC group, whereas no leakage was observed in both the hBMEC+hPC+hAC group and the hBMEC+hBM-MSC+hAC group, and leakage began at 80 seconds (FIG. 6B). The permeability coefficient of 10 kDa FITC-dextran was $3.16\pm0.58\times10^{-5}$ cm/s in the hBMEC group, $1.38\pm0.23\times10^{-5}$ cm/s in the hBMEC+hPC+hAC group, and was $0.96\pm0.13\times10^{-5}$ cm/s in the hBMEC+hBM-MSC+hAC group (FIG. 6C). It may be seen that when recruiting pericytes such as hPCs or hBM-MSCs, and hACs, the permeability coefficient of hBMEC-microvasculature significantly decreases to a level close to the BBB permeability coefficient ($0.31\times10^{-6}$ cm/s) in vivo.

Example 7. Identification of Function and Angiogenesis Excellence of Pericyte in BBB-Like Microvasculature Using hBM-MSCs 7-1. Comparison Between Expressions of Angiogenesis Function-Related Protein of hPCs and hBM-MSCs To identify why hBM-MSCs play a better functional role than hPCs as pericyte in the BBB-like microvasculature on a chip according to the present disclosure, the phenotype of pericyte and the expression of proteins associated with perivascular recruitment thereof were identified via Western blot analysis under single cell culture and co-culture conditions similar to those on a microfluidic angiogenesis chip (hBMEC+hPC, hBMEC+hBM-MSC, hPC, hBM-MSC and hBMEC in a mixture of EGM2 and AM at 1:1). Specifically, under hPC and hBM-MSC alone culture, and co-culture conditions with hBMEC, expressions of proteins important for pericyte function, that is, α-SMA, PDGFR-β, CD13, N-cadherin and desmin, endothelial-specific proteins VE-cadherin, laminin, type IV collagen, and fibronectin as extracellular matrix proteins for basement membrane reconstruction and cell migration were compared with each other. In a similar manner to the microfluidic angiogenesis model, five cell culture groups (hPCs alone, hBM-MSC alone, hPC+hBMEC at 1:6 ratio, hBM-MSC+hBMEC at 1:6 ratio and hBMEC alone) were dispensed such that the final cell density was $2\times10^5$ cells per 100 mm cell culture dish, and the cells were cultured with EGM2 and AM mediums at a ratio of 1:1. On 3 days after the culture, the cells were disrupted and a conditioned medium was collected. The cell lysate was prepared with a lysis buffer (Cell signaling technology, Danvers, MA, USA) containing 1% SDS (Sigma Aldrich) and 2 mM PMSF (Sigma Aldrich). The cell lysate was separated using 6 to 10% SDS-PAGE, transferred to a nitrocellulose membrane, and blocked with 5% skim milk (TBS-T). Thereafter, using α-Tubulin (Sigma Aldrich, 1:4000), α-SMA (Dako, 1:1000), N-cadherin (Invitrogen, 1:1000), PDGFR-β(Abcam, 1:5000), CD13 (Santa Cruz, Dallas, TX, USA, 1:400), desmin (Abcam, 1:3000), VE-cadherin (Cell signaling technology, 1:1000), type IV collagen (Abcam, 1:5000), fibronectin (MP biomedicals, Santa Ana, CA, USA, 1:1000) and laminin-β1 (Santa Cruz, 1:1300) as primary antibodies, the cells were incubated overnight at 4° C. Thereafter, the cells were incubated with goat anti-rabbit HRP (Bio-rad, Hercules, CA, USA, 1:5000) and goat anti-mouse HRP (Bio-rad, 1:3000) as a secondary antibodies for 1 hour, and ECL signal was detected with a Fusion SL 3500 WL imaging system (Vilber Lourmat, Marne-la-Vallee, France).

As a result, functional markers of endothelial recruited-pericytes such as α-SMA, PDGFR-βN-cadherin and CD13 were expressed at a higher level in hBM-MSCs than in hPCs. While these proteins appeared to be downregulated under endothelial co-culture, desmin and VE-cadherin expression patterns did not appear to change (FIG. 7). Thus, it may be seen that the contact of hBM-MSCs or hPCs with the endothelium may cooperate with each other to differentiate the same into a pericyte surrounding the endothelial tube and stabilize the mature capillary network structure.

7-2. Basement Membrane Reconstruction-Related Protein Expression and Angiogenesis Factor Comparison The reconstruction of the basement membrane is very important in the reformation of the mature capillary network. Thus, the expressions of two important components of the basement membrane, that is, laminin and type IV collagen, and fibronectin, as an effector for cell migration and survival of endothelial cells were compared in hPC and hBM-MSC under single culture or co-culture with hBMEC using Western blot analysis. As a result, laminin-β1 is a common subunit expressed in endothelial cells and pericyte, and is mainly expressed in hBMEC, while type IV collagen was expressed more in hPC and hBM-MSC than in hBMEC, thus suggesting the cooperation between endothelial cells and pericyte in basement membrane reconstruction (FIG. 8A). However, fibronectin expression appeared to be highest in the hBM-MSC group, thus suggesting suppression thereof in active cell migration and co-culture in hBM-MSC by surrounding and connecting blood vessels using pericyte. Further, in order to compare the expressions of VEGF, SDF-1α, TGF-β, and HGF, which are major factors related to angiogenesis, the 5 groups of the conditioned medium collected in Example 7-1 and VEGF, TGF-β, HGF and SDF-1α ELISA kit (R&D system, Inc., Minneapolis, MN, USA) were used to perform ELISA analysis. As a result, it was found that the major hypoxia-inducing angiogenesis factors, VEGF and SDF-1α, were expressed only in hBM-MSC. Its expression was found to be significantly down-regulated when hBM-MSC and endothelial cells were co-cultured (FIGS. 8B and 8C). The expression of TGF-β was significantly higher in hBM-MSC than in hPC (FIG. 8D), whereas the expression of HGF was highest in hPC (FIG. 8E). This suggests that hBM-MSCs may act more efficiently in stimulating angiogenesis and surround the endothelial tubesas the pericyte and induce a mature capillary network such that activity thereof may be down-regulated in co-culture with hBMECs.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

REFERENCE NUMERALS

100: blood-vessel formation channel inlet 200: blood-vessel formation channel outlet 300: culture liquid sink 400: culture liquid sink 500: culture liquid sink 600: culture liquid sink 700: first culture channel inlet 800: first culture channel outlet 910: second culture channel inlet 920: second culture channel outlet 110: Fluid pattern guide structure (microstructure)

What is claimed is:

1. An in vitro blood-brain barrier (BBB)-on-a chip comprising:
   a blood-vessel formation channel (C) having a blood-vessel formation channel inlet at one end thereof and a blood-vessel formation channel outlet at the other end thereof;
   a pair of first culture liquid sinks disposed on one side of the blood-vessel formation channel (C) and connected to each other via a sink channel (L1), each first culture liquid sink having a predefined space;
   a pair of second culture liquid sinks disposed on the other side of the blood-vessel formation channel (C) and connected to each other via a source channel (R1), each second culture liquid sink having each predefined space;
   a first culture channel (LO) contacting the sink channel (L1) and having a first culture channel inlet at one end thereof and a first culture channel outlet at the other end thereof; and
   a second culture channel (RO) contacting the source channel (R1) and having a second culture channel inlet at one end thereof and a second culture channel outlet at the other end thereof,
   wherein at a boundary formed (i) between the first culture channel (LO) and the sink channel (L1), (ii) between the sink channel (L1) and the blood-vessel formation channel (C), (iii) between the blood-vessel formation channel (C) and the source channel (R1), and (iv) between the source channel (R1) and the second culture channel (RO), a plurality of microstructures are formed to define a gap therebetween in which biochemical substances received in each of the blood-vessel formation channel (C), the first culture channel (LO), the second culture channel (RO), the sink channel (L1) and the source channel (R1) react with each other,
   wherein the blood-vessel formation channel (C) is consisting essentially of human astrocytes (hACs) and fibrin gel, the sink channel (L1) is consisting essentially of a mixture of endothelial cell growth medium-2 (EGM-2 medium and adipogenic maintenance (AM) medium, a sink channel wall on a side of the blood-vessel formation channel (C) is consisting essentially of human brain microvascular endothelial cells (hBMEC) and human bone marrow-derived mesenchymal stem cells (hBM-MSC), and the second culture channel (RO) is consisting essentially of human lung fibroblasts (hLFs) and fibrinogen.

2. The in vitro blood-brain barrier (BBB)-on-a chip of claim 1, wherein a culture medium is introduced into the pair of first culture liquid sinks and the pair of second culture liquid sinks, wherein a mixture of fibrin gel and feeder cells is injected into the first culture channel inlet or the second culture channel inlet.

3. The in vitro blood-brain barrier (BBB)-on-a chip of claim 1, wherein blood vessel formation occurs in the blood-vessel formation channel (C).

4. The in vitro blood-brain barrier (BBB)-on-a chip of claim 1, wherein the plurality of microstructures are spaced from each other by 100 μm, wherein a size of each gap is 100 μm, wherein a length of each of the blood-vessel formation channel (C), the first culture channel (LO), the second culture channel (RO), the sink channel (L1) and the source channel (R1) is in a range of 3000 to 5000 μm.

5. The in vitro blood-brain barrier (BBB)-on-a chip of claim 1, wherein each of the blood-vessel formation channel (C), the first culture channel (LO), the second culture channel (RO), the sink channel (L1) and the source channel (R1) has a vertical dimension of 100 to 200 μm, wherein a width of each of the blood-vessel formation channel (C), the first culture channel (LO), and the second culture channel (RO) is in a range of 700 to 900 μm, wherein a width of each of the sink channel (L1) and the source channel (R1) is in a range of 600 to 700 μm.

6. The in vitro blood-brain barrier (BBB)-on-a chip of claim 5, wherein hLFs and fibrinogen are contained in a ratio of 3:1 (v/v), wherein EGM-2 medium and AM medium are contained in a ratio of 1:1 (v/v), wherein hBMEC and hBM-MSC are contained in a ratio of 6:1 (n/n).

7. The in vitro blood-brain barrier (BBB)-on-a chip of claim 5, wherein a Vascular Endothelial Growth Factor (VEGF) concentration gradient is formed in a direction from the first culture channel (LO) to the second culture channel (RO).

8. The in vitro blood-brain barrier (BBB)-on-a chip of claim 5, wherein angiogenesis sprouting begins at a wall of the blood-vessel formation channel (C) on one side of the sink channel (L1).

* * * * *